(12) United States Patent
Norikane et al.

(10) Patent No.: US 8,933,208 B2
(45) Date of Patent: Jan. 13, 2015

(54) PHOTO-RESPONSIVE LIQUID CRYSTALLINE COMPOUND AND ITS APPLICATIONS

(75) Inventors: Yasuo Norikane, Tsukuba (JP); Yuki Hirai, Tsukuba (JP); Masaru Yoshida, Tsukuba (JP)

(73) Assignee: National Institute of Advanced Industrial Science and Technology, Tokyo (JP)

( * ) Notice: Subject to any disclaimer, the term of this patent is extended or adjusted under 35 U.S.C. 154(b) by 0 days.

(21) Appl. No.: 13/697,298

(22) PCT Filed: May 10, 2011

(86) PCT No.: PCT/JP2011/002603
§ 371 (c)(1),
(2), (4) Date: Nov. 9, 2012

(87) PCT Pub. No.: WO2011/142124
PCT Pub. Date: Nov. 17, 2011

(65) Prior Publication Data
US 2013/0066068 A1 Mar. 14, 2013

(30) Foreign Application Priority Data

May 10, 2010 (JP) .................. 2010-108325
Nov. 11, 2010 (JP) .................. 2010-252846

(51) Int. Cl.
| C07C 245/08 | (2006.01) |
| C09K 19/24 | (2006.01) |
| C07D 257/10 | (2006.01) |
| C09K 19/34 | (2006.01) |
| G02F 1/135 | (2006.01) |
| G02F 1/01 | (2006.01) |
| G02F 1/1333 | (2006.01) |

(52) U.S. Cl.
CPC ............. *C09K 19/24* (2013.01); *C07D 257/10* (2013.01); *C09K 19/3488* (2013.01); *G02F 1/1354* (2013.01); *G02F 1/0126* (2013.01); *G02F 1/133362* (2013.01); *G02F 2001/1355* (2013.01); *G02F 2202/14* (2013.01)
USPC .......................................... 534/552; 534/550

(58) Field of Classification Search
CPC ................................................... C07C 291/00
USPC ................................................... 534/550, 552
See application file for complete search history.

(56) References Cited

FOREIGN PATENT DOCUMENTS

JP 2005-089371 A 4/2005

OTHER PUBLICATIONS

Norikane et al., Chemical Communications (2011), 47, 1770-1772 (first published on the web Dec. 2, 2010).*

Norikane, J. Org. Chem., vol. 68, No. 22, p. 8291-8304 (2003).*
Notification Concerning Transmittal of International Preliminary Report on Patentability (PCT/IB/326) and International Preliminary Report on Patentability (PCT/IB/373) and Written Opinion of the International Searching Authority (PCT/ISA/237) in International Patent Application No. PCT/JP2011/002603, dated Nov. 22, 2012.
Notification of Transmittal of Translation of the International Preliminary Report on Patentability (PCT/IB/338) and English-language translation of International Preliminary Report on Patentability (PCT/IB/373) and Written Opinion of the International Searching Authority (PCT/ISA/237) in International Patent Application No. PCT/JP2011/002603, dated Dec. 20, 2012.
Shimizu et al., "Calamitic and discotic mesophases formed by kinetically controlled rod-disc alternation of molecular shape in a triphenylene-azobenzene mesogenic system," Chem. Comm, pp. 1676-1677 (2003).
Norikane et al., "Novel Crystal Structure, Cis-Trans Isomerization, and Host Property of Meta-Substituted Macrocyclic Azobenzenes with the Shortest Linkers," J. Org. Chem., vol. 68, No. 22, pp. 8291-8304 (2003).
Westphal et al., "Synthesis and Optical/Thermal Behavior of New Azo Photoisomerizable Discotic Liquid Crystals," Macromolecules, vol. 43, No. 3, pp. 1319-1328 (2010).

(Continued)

*Primary Examiner* — Yong Chu
*Assistant Examiner* — Sonya Wright
(74) *Attorney, Agent, or Firm* — Venable LLP; Keith G. Haddaway; Daniel A. Kopp

(57) ABSTRACT

The purpose of the present invention is to provide novel liquid crystalline compounds that are capable of inducing phase transition by a light stimulus and are useful in the display, optoelectronics, and photonics field. The present invention relates to the liquid crystalline compounds represented by general formula (1):

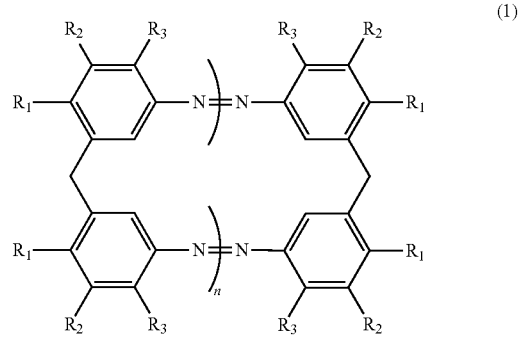

wherein $R^1$, $R^2$ and $R^3$ are independently selected from the group consisting of hydrogen, alkyl, alkoxyl, alkoxycarbonyl, alkoxycarbonyloxy, alkanoyl, alkanoyloxy, alkoxyphenyl, and N-alkylaminocarbonyl, and n is an integer.

4 Claims, 10 Drawing Sheets

(56) References Cited

OTHER PUBLICATIONS

Ringsdorf et al., "Synthesis and properties of azo-containing discotic liquid crystals," Polymer Preprints, vol. 33, No. 1, pp. 1202-1203 (1992).

Ikeda et al., "Effect of structure of photoresponsive molecules on photochemical phase transition of liquid crystals IV. Photochemical phase transition behaviors of photochromic azobenzene guest/polymer liquid crystal host mixtures," Molecular Crystals and Liquid Crystals, vol. 188, pp. 223-233 (1990).

Muri et al., "Shape-Switchable Azo-Macrocycles," Eur. J. Org. Chem., pp. 2562-2575 (2009).

Artal et al., "Synthesis and mesogenic properties of novel board-like liquid crystals," Journal of Materials Chemistry, 2001, vol. 11, pp. 2801-2807.

Laschat et al., "Discotic Liquid Crystals: From Tailor-Made Synthesis to Plastic Electronics," Angew. Chem. Int. Ed., 2007, vol. 46, pp. 4832-4887.

Tamaoki et al., "[202](4,4') Azobenzenophane. Synthesis, Structure, and Cis-Trans Isomerization," Tetrahedron, 1990 vol. 46, pp. 5931-5942.

* cited by examiner

PHOTO-RESPONSIVE LIQUID CRYSTALLINE COMPOUND AND ITS APPLICATIONS

TECHNICAL FIELD

The present application relates to a photo-responsive liquid crystalline compound and applications of the compound.

BACKGROUND ART

Along with development of highly computerized society, many investigations for applying optical technology to transmission, processing and recording of information have been conducted, in order to efficiently treat a large amount of information. In this context, liquid crystalline compounds are expected to be significantly useful material, which can control properties of light such as wavelength, transmittance and polarization in an adjustable manner.

It is known that liquid crystalline compounds are utilized in optical materials such as nonlinear optical materials and photochromic materials. Displays on which characters and images are displayed and optical compensator are known as manufactured products made with the optical material. On the other hand, the liquid crystalline compounds are known as raw material of fiber or reinforced plastics for example, in addition to the optical material. Further, the liquid crystalline compounds are expected to be applied to tribology material, electrically conductive material, semiconductive material, and luminescent material in which extraordinary properties of the liquid crystalline compounds are utilized.

Liquid crystalline compounds are generally classified into two categories. One of the categories is calamitic liquid crystal composed of rod-like molecules, and the other is discotic liquid crystal composed of disc-like molecules. As an example of practical application, in existing liquid crystalline displays, the rod-like liquid crystalline molecules are used in the part for performing optical switching, and the discotic liquid crystalline compound are used in an optical compensation film (a phase difference plate).

Discotic (disc-like) liquid crystalline compounds having a broad π-conjugated plane as a core forms a columnar (column-like) phase in which the disc-like compounds are stacked to each other in a self-organizing manner. In the columnar phase, the π-conjugated planes are accumulated to the center of the column in one dimensional manner, to form one-dimensional channel. This one-dimensional channel provides high charge transporting properties, which are comparable to those of an organic single crystal and amorphous silicon. Besides, the discotic liquid crystalline compounds have been extensively investigated over the world, as a fundamental material for next-generation printable electronics. This is because superior properties of the discotic liquid crystalline compounds such as self-orienting properties, solubility and flexibility are significantly advantageous for device production in a simple solution process.

Discotic liquid crystalline compounds are in disc-like shapes and have a central core (cyclic core) and radially extending side-arms attached to the core. Orientation of the disc-like compounds causes optical anisotropy (polarizability), electronic anisotropy (electron or charge transporting properties), and mechanical anisotropy (viscosity). By making full use of such properties, it is expected to utilize the discotic liquid crystalline compound as display material, optoelectronic material, photonic material and tribologic material. Further, negative optical anisotropy, which is the characteristic property of the disc-like molecules, is most generally utilized in an optical compensation film for liquid crystalline display, at the present time. Thus, there is a great need in the present industrial community to develop novel discotic liquid crystal having novel optical properties and/or processability.

The above-describe various properties are caused by the orientation state of the liquid crystalline molecules. Thus, it becomes possible to optically switch the charge transporting properties of the liquid crystalline molecules, if the orientation state of the liquid crystalline molecules can be controlled by phase transition caused by a stimulus of light in an adjustable manner. Such light stimulus-responsive liquid crystalline material is useful as information recording material in optical memories, for example. However, phase transition of discotic liquid crystalline phase caused by light has not been reported until now. Shimizu et al reported a discotic liquid crystalline compound in which photosensitive azobenzenes are attached to the disc-like compound (triphenylene) as the side arms (see NPL 1). However, the structural change of the whole molecule caused by isomerization of azobenzene moieties is not large enough to induce the phase transition, because the photo-responsive moieties are introduced in the side arms.

Further, organic compounds having a photo-induced phase transition property between a crystalline (solid) phase and an isotropic phase have not been found yet.

CITATION LIST

Non-Patent Literature

NPL1: Yo Shimizu, Atshiko kurobe, Hirosato Monobe, Naohiro Terasawa, Kenji Kiyohara, Kingo Uchida, Chem. Comm., 2003, 1676-1677.

NPL2: Y. Norikane, K. Kitamoto, N. Tamaoki, J. Org. Chem., 2003, 68, 8291-8304.

SUMMARY OF INVENTION

Technical Problem

Thus, there is a problem that more remarkable change in the molecular shape must be induced by a stimulus of light, in order to accomplish phase transition of the liquid crystalline compound. Accordingly, taking note of macrocyclic azobenzenes in the present invention, it is intended to impart photoresponsivity to the liquid crystalline core part itself having a disc-like shape, apart from the conventional molecular design. The present inventors found that macrocyclic azobenzenes without side arms form a columnar structure in which the molecules were piled up one dimensionally in the crystalline state, and the macrocyclic azobenzenes without side arms exhibit step-wise cis-trans isomerization by exposure to light in the solution state (see NPL 2).

The object of the present invention is to provide novel liquid crystalline compounds capable of controlling their phase transition by the stimulus of light in an adjustable manner. Further, the object of the present invention is to provide novel liquid crystalline compounds useful in the technical fields of display, optoelectronics and photonics.

Solution to Problem

As a result of intensive study of disc-like discotic liquid crystalline compounds capable of phase transition by a stimulus of light, the present inventors have found that compounds having a cyclic core in which azobenzenes are connected in a cyclic manner and radially extending side arms attached to the core exhibit phase transition of discotic phases by light, and such compounds also exhibit phase transition from crystal to liquid. Then, the present invention was brought to perfection.

That is, the present application provides the following inventions.

<1> A liquid crystalline compound represented by general formula (1):

[Chemical Formula 1]

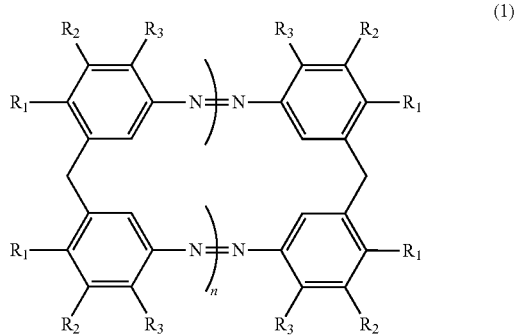

(1)

wherein:

$R^1$, $R^2$ and $R^3$ are independently selected from the group consisting of hydrogen, alkyl, alkoxyl, alkoxycarbonyl, alkoxycarbonyloxy, alkanoyl, alkanoyloxy, alkoxyphenyl, and N-alkylaminocarbonyl; and n represents an integer;

with the proviso that the case where all of $R^1$, $R^2$ and $R^3$ are hydrogen is excluded.

<2> The liquid crystalline compound according to item <1>, wherein n is an integer of 1 to 4.

<3> The liquid crystalline compound according to item <1>, which undergoes phase transition by exposure to ultraviolet light or visible light.

<4> The liquid crystalline compound according to item <1> exhibiting a discotic liquid crystalline phase.

<5> The liquid crystalline compound according to item <1>, which undergoes reversible phase transition between a crystalline phase and an isotropic phase by exposure to ultraviolet light or visible light.

<6> An optical element comprising the liquid crystalline compound according to any of items <1> to <5>.

<7> A photosensitive material comprising the liquid crystalline compound according to any of items <1> to <5>.

<8> The photosensitive material according to item <7> in a form of photo-patternable material or photosensitive ink.

Advantageous Effects of Invention

The present invention permits not only the phase transition of the liquid crystal induced by light, but also control of the transition temperature of the liquid crystalline phase by structural change of the molecules. That is, the present invention can provide liquid crystalline material and liquid crystalline compounds capable of controlling properties of the liquid crystal in a wide range. Moreover, the compounds of the present invention can undergo reversible phase transition between a crystalline phase and an isotropic phase by a stimulus of light. In view of the above, the compounds of the present invention are expected to be applied to photo-switchable optical elements, organic semiconductor elements, and photosensitive material such as photo-patternable material or photosensitive ink.

DESCRIPTION OF EMBODIMENTS

Figure 1A:
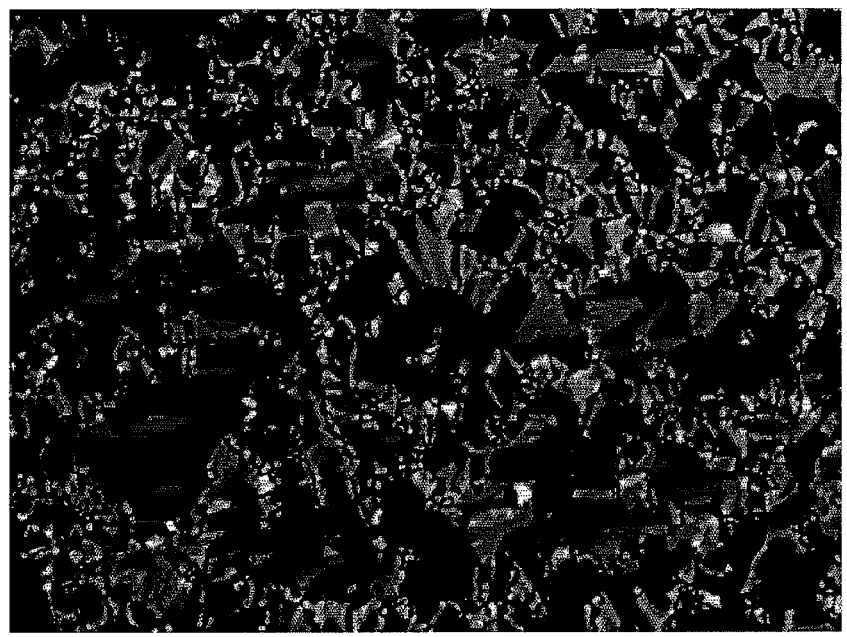
FIG. 1A shows a polarizing optical micrograph of Liquid Crystalline Compound 1 at a temperature of 120° C.

The liquid crystalline compounds of the present invention are represented by the general formula described below.

[Chemical Formula 2]

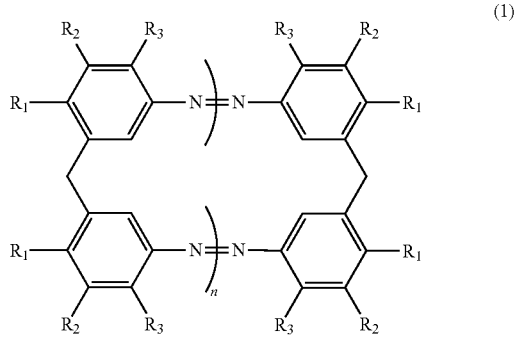

(1)

In general formula (1) shown above, each of $R_1$, $R_2$ and $R_3$ is independent and may be the same or different, in each occurrence. Each of $R_1$, $R_2$ and $R_3$ represents hydrogen, alkyl, alkoxyl, alkoxycarbonyl, alkoxycarbonyloxy, alkanoyl, alkanoyloxy, alkoxyphenyl, or N-alkylaminocarbonyl. The alkyl chain moieties in the above-described substituents may be either linear or branched. However, at least one of $R_1$, $R_2$ and $R_3$ is not hydrogen in the present invention. In other words, the compound in which all of $R_1$, $R_2$ and $R_3$ are hydrogen falls outside of the present invention.

Further, in general formula (1), n is an integer. Here, the compounds having general formula (1) can be generally synthesized by reductive cyclization of precursor dinitro compounds (methylene-bridged dimerized nitrobenzene derivatives). In the synthesis, the compound having general formula (1) is mainly obtained as a mixture of compounds wherein n is in a range of 1 to 10. The compound corresponding to each of n can be isolated by gel permeation chromatography of the resultant mixture. In the compounds having general formula (1), the greater n is, the lower the solubility of the corresponding compound in organic solvent is. Moreover, taking into account the stereochemical structure of the compounds having general formula (1), it is considered that, if n is 5 or more, it becomes difficult to achieve disc-like structure of the molecule, and thereby liquid crystalline property of the molecule decreases in principle. Therefore, in the present invention, n is desirably an integer from 1 to 4.

Further, dinitro compounds (methylene-bridged dimerized nitrobenzene derivatives), which are precursors of the compounds having general formula (1), can be produced by a method comprising the steps of: (a) dimerizing nitrobenzene derivatives with formaldehyde; and (b) introducing substituents to the dimerized nitrobenzene derivatives, for example. Alternatively, the dinitro compounds (methylene-bridged dimerized nitrobenzene derivatives) may be produced by a method comprising the steps of: (a') introducing substituents to nitrobenzene derivatives; and (b') dimerizing the substituted nitrobenzene derivatives with formaldehyde.

Preferred specific examples of the liquid crystalline compounds of the present invention are compounds wherein $R_1$ is alkoxyl, $R_2$ and $R_3$ are hydrogen, and n is an integer of 1 to 4. More preferred specific examples are compounds wherein $R_1$ is dodecyloxy, $R_2$ and $R_3$ are hydrogen, and n is an integer of 1 to 4. Typical examples of the liquid crystalline compounds of the present invention represented by general formula (1) will be demonstrated in Examples set forth below, however, the liquid crystalline compounds of the present invention are not limited by such typical examples.

The liquid crystalline compounds of the present invention exhibit a discotic liquid crystalline phase, since the macrocyclic azobenzene acts as a mesogen. Further, in the liquid crystalline compounds of the present invention, phase transition of the liquid crystalline phases occurs by isomerization of azo bonding (—N=N—) by exposure to ultraviolet or visible light. The wavelength of the light which induces the phase transition of the liquid crystalline phases varies according to the value of n in general formula (1), and electronic and steric effects of the side arms ($R_1$, $R_2$ and $R_3$).

Optical elements such as photo-controllable TFT element or photo-controllable liquid crystalline display can be produced by using the liquid crystalline compounds of the present invention.

Moreover, the present inventors have found that the liquid crystalline compounds of the present invention carry out reversible phase transition between a crystalline phase and an isotropic phase by a stimulus of light at room temperature (25° C.). The wavelength of the light which induces this phase transition varies according to the value of n in general formula (1), and electronic and steric effects of the side arms ($R_1$, $R_2$ and $R_3$).

Photosensitive material capable of repetitive use can be produced by using the liquid crystalline compounds of the present invention, since the phase transition between the crystalline phase and the isotropic phase of the liquid crystalline compounds of the present invention is reversible. For example, photo-patterning material capable of repetitive use can be produced by using the liquid crystalline compounds of the present invention. Alternatively, photosensitive ink capable of transfer by exposure to light can be produced by using the liquid crystalline compounds of the present invention, which can substitute thermal transfer ink suffering from a limitation of resolution due to a thermal process. Further, the liquid crystalline compounds of the present invention can be applied to adhesion technique capable of photo-induced detachment according to change in viscosity (coefficient of friction).

EXAMPLES

Example 1

Synthesis of Liquid Crystalline Compound 1 (n=1, $R_1$=$OC_{12}H_{25}$, $R_2$=H and $R_3$=H) and Liquid Crystalline Compound 2 (n=2, $R_1$=$OC_{12}H_{25}$, $R_2$=H and $R_3$=H)

[Chemical Formula 3]

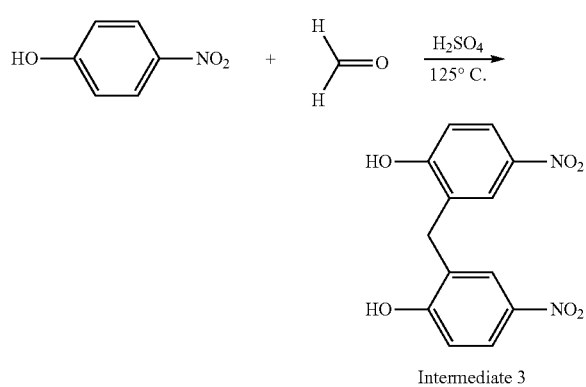

(1) Synthesis of Intermediate 3

Para-nitrophenol (27.8 g, 200 mmol) was dissolved in 5 mL of water by heating to a temperature of 80° C. and stirring. To this solution was added 10 mL of concentrated sulfuric acid and 10 mL of aqueous solution of formaldehyde (35%), raising the temperature to 125° C. and continue stirring for 1 hour. After confirming disappearance of para-nitrophenol by thin layer chromatography (TLC), the reaction mixture was allowed to cool to room temperature, and solid was precipitated by pouring distilled water to the reaction mixture. The resultant solids were collected by filtration and dispersed in 5% NaOH aqueous solution. Insoluble material was removed by filtration. The resultant basic aqueous solution was acidified by hydrochloric acid to precipitate solid. The precipitated solids were collected by filtration, washed with distilled water, and dried under vacuum, to obtain Intermediate 3 (pale yellow solid, yield: 26.4 g, 91%).

[Chemical Formula 4]

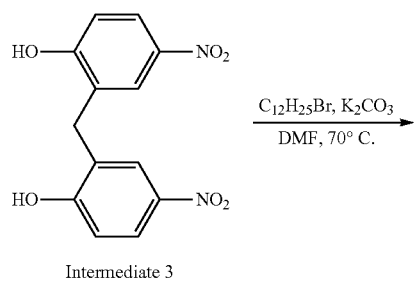

Intermediate 3

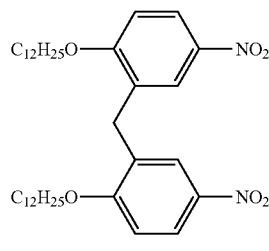

Intermediate 4

(2) Synthesis of Intermediate 4

A mixture of Intermediate 3 (2.9 g, 10 mmol), 1-bromododecane (7.5 g, 30 mmol), potassium carbonate (6.9 g, 50 mmol) and N,N-dimethyl formamide (DMF, 50 mL) was heated to a temperature of 80° C. and stirred for 4 hours, under nitrogen atmosphere. After confirming disappearance of Intermediate 3 by TLC, distilled water was added to the reaction mixture and extracted with hexane. Combined organic phase was washed once with distilled water, and once with saturated aqueous solution of sodium chloride. Subsequently, magnesium sulfate was added to the organic phase to dry it. After solids were filtered off, solvent was removed by evaporation under reduced pressure. The target compound was separated by silica gel column chromatography in which mixed liquid of hexane and chloroform of 1/1 was used as an eluent, and then solvent was removed by evaporation under reduced pressure to obtain pure Intermediate 4 (white crystal, yield: 3.2 g, 51%).

[Chemical Formula 5]

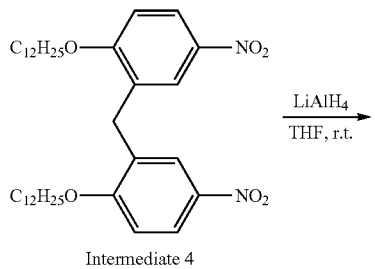

Intermediate 4

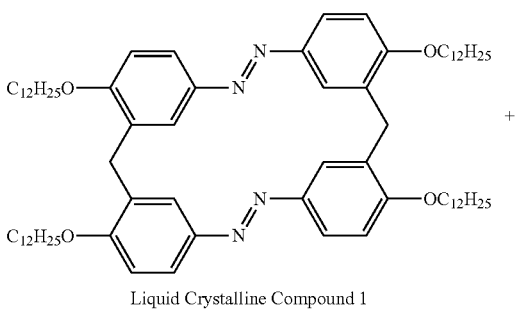

Liquid Crystalline Compound 1

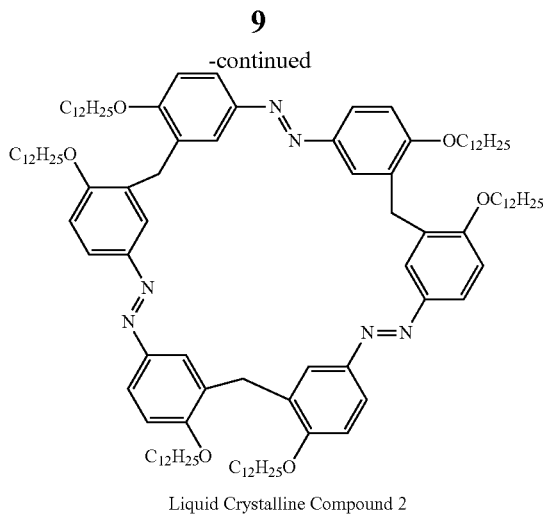

Liquid Crystalline Compound 2

(3) Synthesis of Liquid Crystalline Compounds 1 and 2

Intermediate 4 (1.0 g, 1.6 mmol) was dissolved in 300 mL of anhydrous tetrahydrofuran (THF). To this solution, 9.0 mL of solution of lithium aluminum hydride in anhydrous THF (1.0 mol/L) was added at room temperature over about 20 minutes, and then stirred at a temperature of 40° C. for 3 hours. To the reaction solution was added 200 mL of distilled water, and most of THF was removed by evaporation under reduced pressure. The obtained residue was extracted with ethyl acetate. Combined organic phase was washed once with distilled water, and once with saturated aqueous solution of sodium chloride. Subsequently, magnesium sulfate was added to the organic phase to dry it. After solids were filtered off, solvent was removed by evaporation under reduced pressure. The obtained residue was purified by silica gel column chromatography in which mixed liquid of hexane and ethyl acetate of 20/1 was used as an eluent, to obtain a mixture containing a plurality of cyclic oligomers. The mixture was further separated by gel permeation chromatography to obtain Liquid Crystalline Compound 1 (orange solid, yield: 6.4 mg, 0.7%) which was a cyclic dimer, and Liquid Crystalline Compound 2 (orange grease, yield: 13.0 mg, 1.4%) which was a cyclic trimer.

Liquid Crystalline Compound 1
TLC: $R_f$=0.31 (CHCl$_3$-Hexane, 1:1);
$^1$H NMR (400 MHz, CDCl$_3$): δ 8.06 (d, J=2.4 Hz, 4H), 7.62 (dd, J=8.7 Hz, J$_2$=2.4 Hz, 4H), 6.92 (d, J=8.8 Hz, 4H), 4.21 (s, 4H), 4.05 (t, J=6.5 Hz, 8H), 1.87 (m, 8H), 1.22-1.72 (m, 80H), 0.90 (t, J=6.7 Hz, 12H);
$^{13}$C NMR (100 MHz, CDCl$_3$): δ 157.6, 146.2, 127.5, 127.1, 118.7, 110.3, 67.5, 30.9, 28.7, 28.6, 28.4, 28.3, 28.2, 25.0, 23.8, 21.6, 13.1;
MS (MALDI): m/z 1125.90 (calc. [M+H]$^+$=1125.90)

Liquid Crystalline Compound 2
TLC: $R_f$=0.31 (CHCl$_3$-Hexane, 1:1);
$^1$H NMR (400 MHz, CDCl$_3$): δ 7.71 (dd, J=8.6 Hz, J$_2$=2.4 Hz, 6H), 7.64 (d, J=2.4 Hz, 6H), 6.91 (d, J=8.8 Hz, 6H), 4.09 (s, 4H), 4.00 (t, J=6.4 Hz, 12H), 1.76 (m, 12H), 1.21-1.44 (m, 120H), 0.90 (t, J=6.7 Hz, 18H);
$^{13}$C NMR (100 MHz, CDCl$_3$): δ 159.1, 146.8, 130.0, 124.3, 122.9, 111.0, 68.4, 32.1, 29.9, 29.8, 29.7, 29.6, 29.5, 29.4, 29.3, 26.2, 22.8, 14.3;
MS (MALDI): m/z 1688.38 (calc. [M+H]$^+$=1688.35)

Structure of Liquid Crystalline Phase of Liquid Crystalline Compounds 1 and 2

Figure 1B:
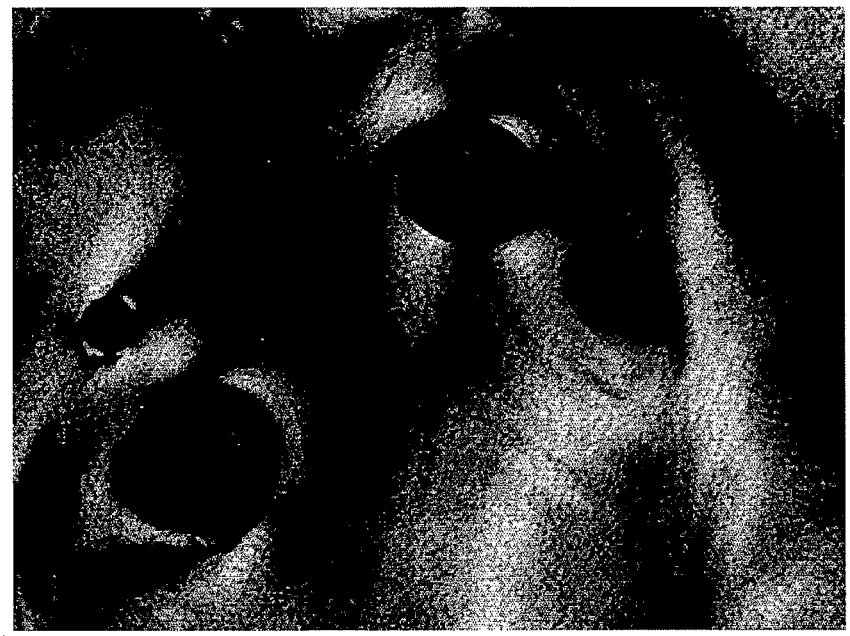
FIG. 1B shows a polarizing optical micrograph of Liquid Crystalline Compound 2 at room temperature.

Liquid Crystalline Compounds 1 and 2 obtained as described above were filled into a glass sandwich cell and observed by a polarizing optical microscope equipped with a hot stage. FIG. 1A shows a polarizing optical micrograph of Liquid Crystalline Compound 1 at a temperature of 120° C., and FIG. 1B shows a polarizing optical micrograph of Liquid Crystalline Compound 2 at room temperature. Both of Liquid Crystalline Compounds 1 and 2 exhibited birefringence in crossed nicols observation, and had flowability. Especially, Liquid Crystalline Compound 1 exhibited fan texture which is characteristic of a smectic phase (FIG. 1A).

Figure 2A:
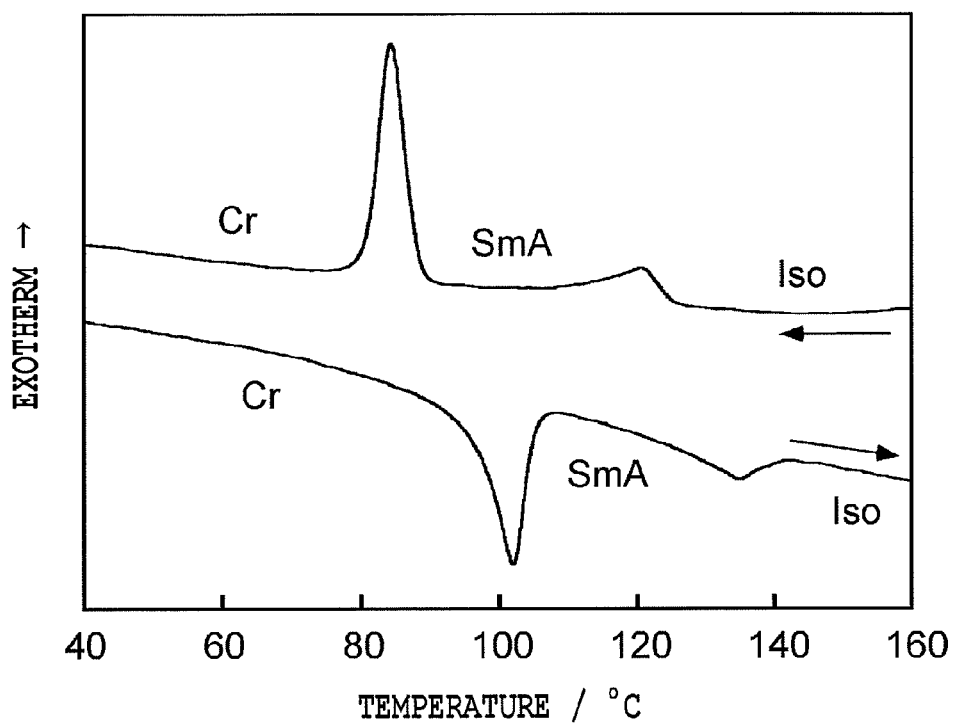
FIG. 2A shows a chart of differential scanning calorimetry (DSC) of Liquid Crystalline Compound 1.
Figure 2B:
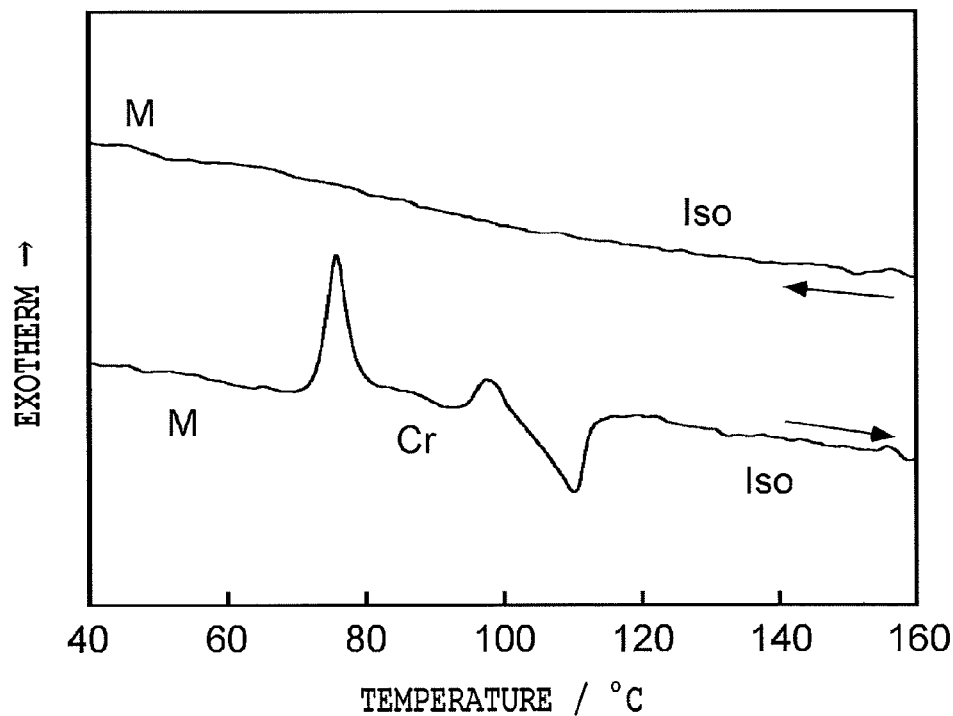
FIG. 2B shows a chart of DSC of Liquid Crystalline Compound 2.

Thermal behavior of Liquid Crystalline Compounds 1 and 2 was analyzed by differential scanning calorimetry (DSC). The results are shown in FIG. 2A (Liquid Crystalline Compound 1) and FIG. 2B (Liquid Crystalline Compound 2). Liquid Crystalline Compound 1 exhibited a liquid crystalline phase in a range of 121° C. to 84° C. in the course of cooling. Liquid Crystalline Compound 2 exhibited a liquid crystalline phase in a range of not higher than 60° C. in the course of cooling.

Figure 3A:
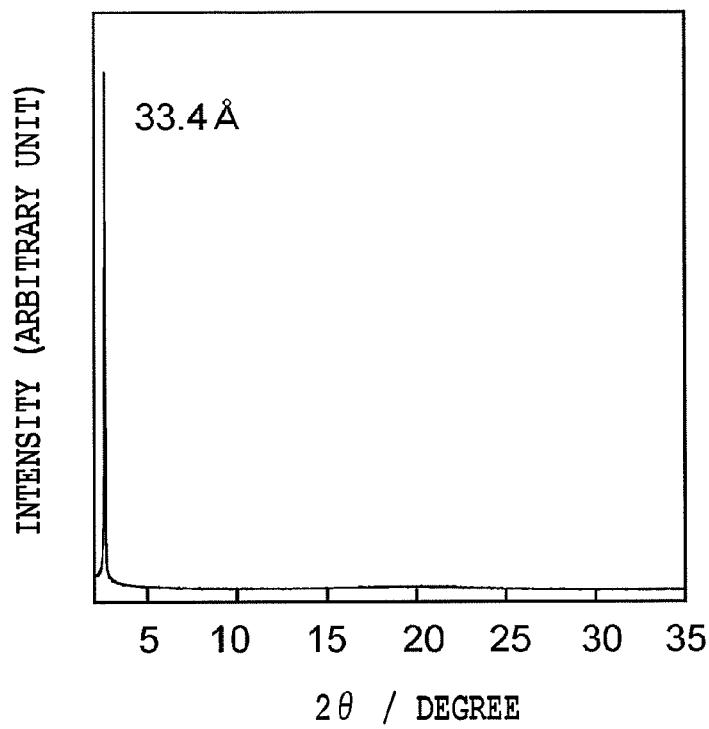
FIG. 3A shows an x-ray diffraction pattern of Liquid Crystalline Compound 1 at a temperature of 110° C.
Figure 3B:
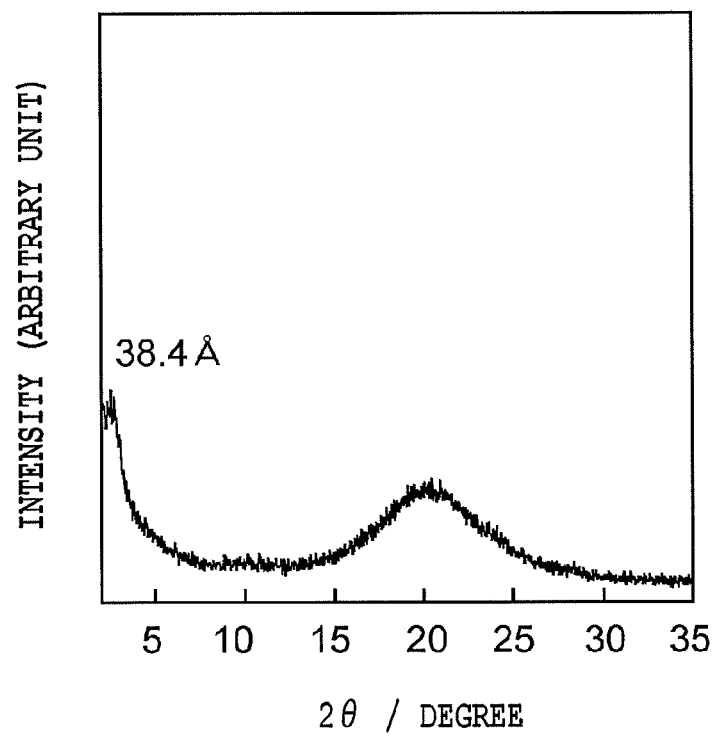
FIG. 3B shows an x-ray diffraction pattern of Liquid Crystalline Compound 2 at room temperature.

Then, the liquid crystalline phases of Liquid Crystalline Compounds 1 and 2 were analyzed by x-ray diffraction method, at a temperature where each of compounds exhibited the liquid crystalline phase. The resultant x-ray diffraction patterns are shown in FIG. 3A (Liquid Crystalline Compound 1) and FIG. 3B (Liquid Crystalline Compound 2). In the x-ray diffraction measurement of the liquid crystalline phase of Liquid Crystalline Compound 1, a sharp diffraction peak was observed, which corresponds to a periodic structure of a periodic lattice of 33 Å that is slightly shorter than the molecular length of 35 Å. From this result, it was determined that the liquid crystalline phase of Liquid Crystalline Compound 1 is a smectic A phase in which alkyl chains overlap partially. On the other hand, only a broad peak corresponding to the molecular length of 38 Å, and a broad halo corresponding to molten alkyl chains were observed in the x-ray diffraction measurement of the liquid crystalline phase of Liquid Crystalline Compound 2. From this result, it was seen that the liquid crystalline phase of Liquid Crystalline Compound 2 is a mesophase having a low order.

Photoreactivity of Liquid Crystalline Compounds 1 and 2

Figure 4A:
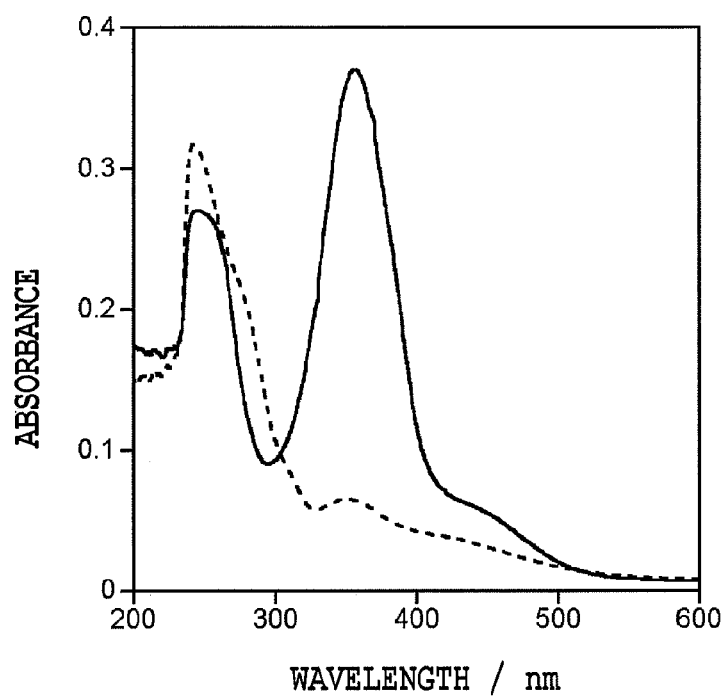
FIG. 4A shows ultraviolet-visible absorption spectra of a solution of Liquid Crystalline Compound 1 in chloroform, before and after exposure to ultraviolet light.
Figure 4B:
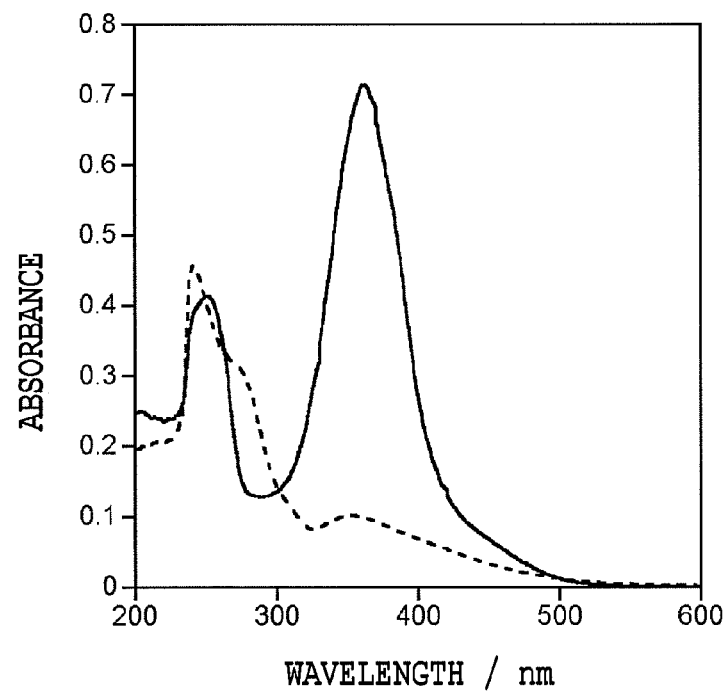
FIG. 4B shows ultraviolet-visible absorption spectra of a solution of Liquid Crystalline Compound 2 in chloroform, before and after exposure to ultraviolet light.

Ultraviolet-visible absorption spectra of solutions of Liquid Crystalline Compounds 1 and 2 in chloroform (1.0×10$^{-5}$ M) were measured before and after exposure to ultraviolet light (wavelength 365 nm). The results are shown in FIG. 4A (Liquid Crystalline Compound 1) and FIG. 4B (Liquid Crystalline Compound 2). In FIGS. 4A and 4B, solid lines show the spectra before the exposure to ultraviolet light, and broken lines show the spectra after the exposure to ultraviolet light. For both of Liquid Crystalline Compounds 1 and 2, absorption around a wavelength of 350 nm caused by trans isomers of azobenzenes was reduced, and weak absorption in a longer wavelength region of a wavelength of 500 nm or more was increased, after the exposure to ultraviolet light. Almost the same change was observed in Liquid Crystalline Compounds 1 and 2 in a thin-film form containing no solvent. From this result, it becomes evident that Liquid Crystalline Compounds 1 and 2 exhibit photoisomerization efficiently by the exposure to the ultraviolet light.

Photoinduced Phase Transition between a Liquid Crystalline Phase and Isotropic Phase of Liquid Crystalline Compounds 1 and 2

Figure 5A:
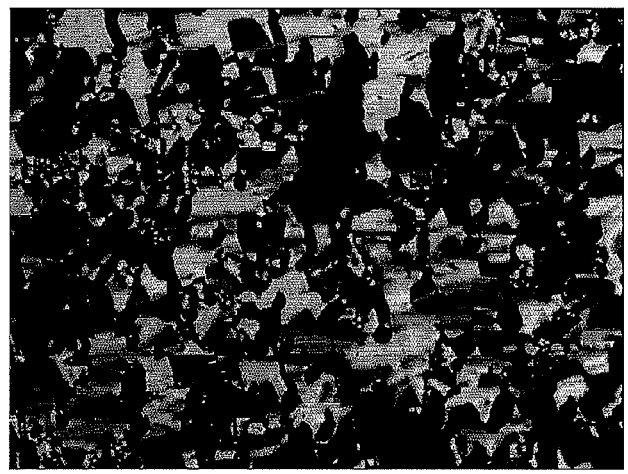
FIG. 5A shows a polarizing optical micrograph of Liquid Crystalline Compound 1 at a temperature of 120° C. before exposure to ultraviolet light.
Figure 5B:
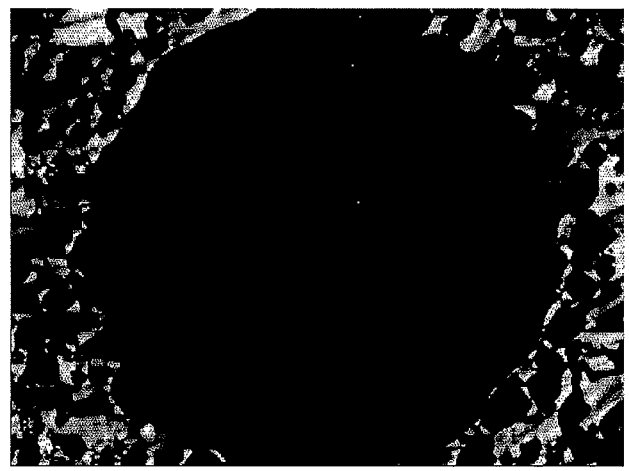
FIG. 5B shows a polarizing optical micrograph of Liquid Crystalline Compound 1 at a temperature of 120° C. just after the exposure to ultraviolet light.
Figure 5C:
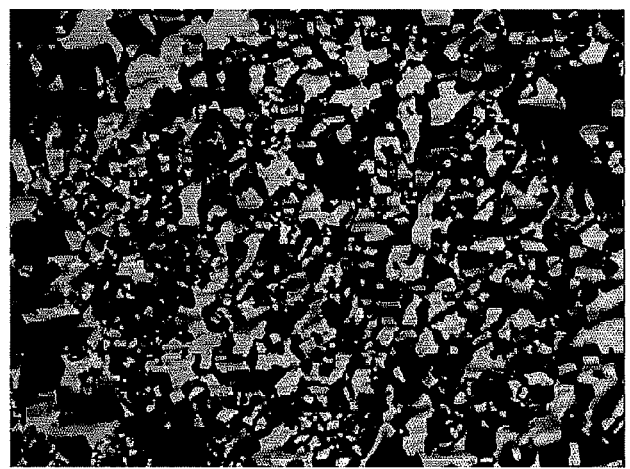
FIG. 5C shows a polarizing optical micrograph of Liquid Crystalline Compound 1 at a temperature of 120° C. ten seconds after the exposure to ultraviolet light.
Figure 6A:
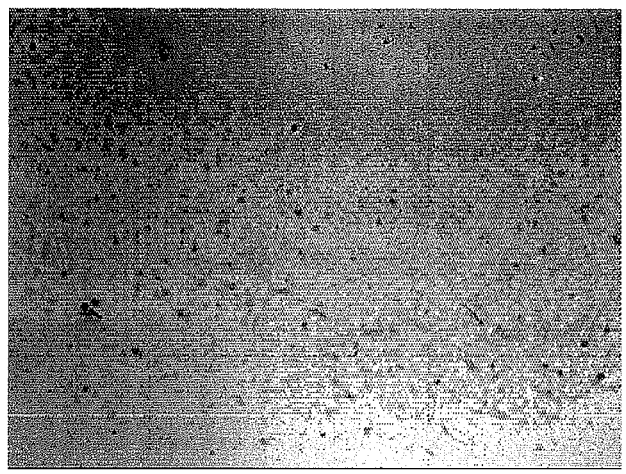
FIG. 6A shows a polarizing optical micrograph of Liquid Crystalline Compound 2 at a temperature of 25° C. before exposure to ultraviolet light.
Figure 6B:
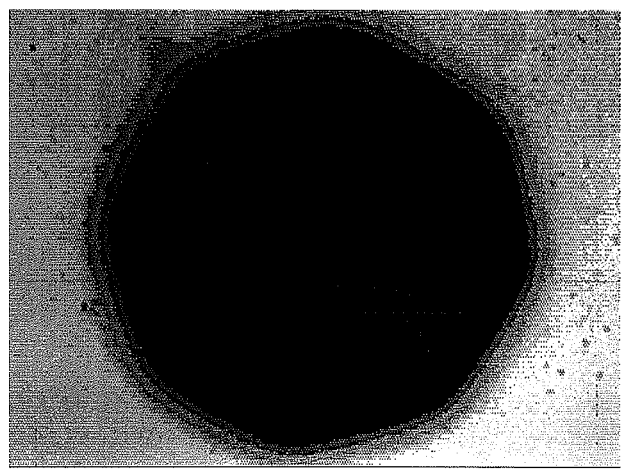
FIG. 6B shows a polarizing optical micrograph of Liquid Crystalline Compound 2 at a temperature of 25° C. just after the exposure to ultraviolet light.
Figure 6C:
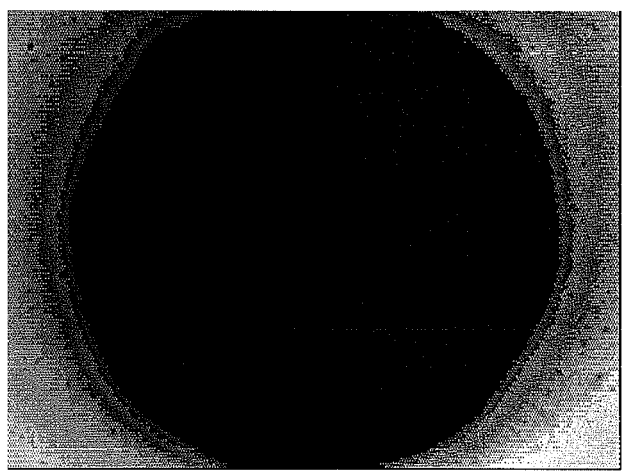
FIG. 6C shows a polarizing optical micrograph of Liquid Crystalline Compound 2 at a temperature of 25° C. ten seconds after the exposure to ultraviolet light.

Liquid Crystalline Compounds 1 and 2 were filled into a glass sandwich cell and exposed to ultraviolet light under observation with polarizing optical microscope. FIG. 5A is a polarizing optical micrograph of Liquid Crystalline Compound 1 at a temperature of 120° C. before exposure to ultraviolet light, FIG. 5B is a polarizing optical micrograph of Liquid Crystalline Compound 1 at a temperature of 120° C. just after the exposure to ultraviolet light, and FIG. 5C is a polarizing optical micrograph of Liquid Crystalline Compound 1 at a temperature of 120° C. ten seconds after the exposure to ultraviolet light. FIG. 6A is a polarizing optical micrograph of Liquid Crystalline Compound 2 at a temperature of 25° C. before exposure to ultraviolet light, FIG. 6B is a polarizing optical micrograph of Liquid Crystalline Compound 2 at a temperature of 25° C. just after the exposure to ultraviolet light, and FIG. 6C is a polarizing optical micrograph of Liquid Crystalline Compound 2 at a temperature of 25° C. ten seconds after the exposure to ultraviolet light.

In both of Liquid Crystalline Compounds 1 and 2, isomerization and phase transition from a liquid crystalline phase to an isotropic phase (Iso) were induced by the exposure of ultraviolet light, and a dark field was observed in crossed nicols observation.

Here, Liquid Crystalline Compound 1 re-established the liquid crystalline phase as shown in FIG. 5C, within a few seconds after the exposure to ultraviolet light. This phenomenon was caused by thermal retro-isomerization, since the temperature of establishing the liquid crystalline phase of Liquid Crystalline Compound 1 is a high temperature around 100° C. On the other hand, Liquid Crystalline Compound 2 maintained the photo-induced isotropic state after the exposure to ultraviolet light, as shown in FIG. 6C. This phenomenon was caused by suppression of thermal retro-isomerization, since the temperature of establishing the mesophase of Liquid Crystalline Compound 2 is around room temperature. Photoinduced Phase Transition Between a Crystalline Phase and Isotropic Phase of Liquid Crystalline Compounds 1 and 2

Figure 7A:
FIG. 7A shows a polarizing optical micrograph of Liquid Crystalline Compound 1 at a temperature of 25° C.
Figure 7B:
FIG. 7B shows a polarizing optical micrograph of Liquid Crystalline Compound 1 at a temperature of 25° C. just after the first exposure to ultraviolet light.
Figure 7C:
FIG. 7C shows a polarizing optical micrograph of Liquid Crystalline Compound 1 which have been heated to a temperature of 100° C. then cooled to a temperature of 25° C. after the first exposure to ultraviolet light.
Figure 7D:
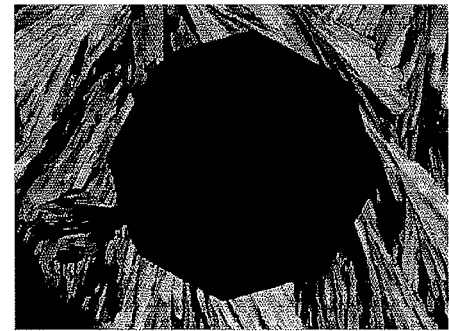
FIG. 7D shows a polarizing optical micrograph of Liquid Crystalline Compound 1 at a temperature of 25° C. after the second exposure to ultraviolet light.
Figure 8A:
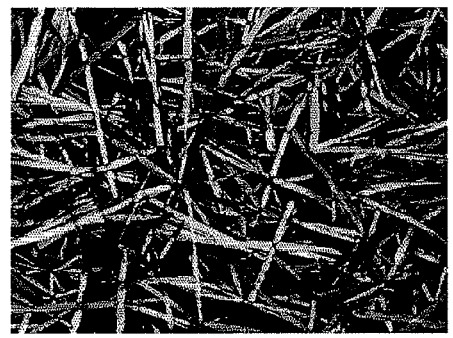
FIG. 8A shows a polarizing optical micrograph of Liquid Crystalline Compound 2 at a temperature of 25° C.
Figure 8B:
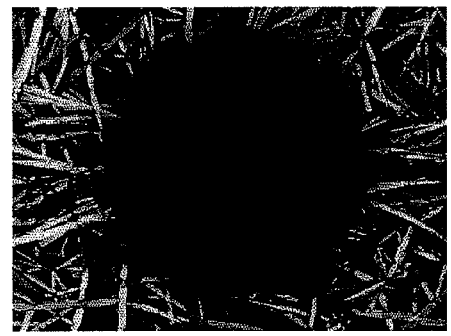
FIG. 8B shows a polarizing optical micrograph of Liquid Crystalline Compound 2 at a temperature of 25° C. just after the first exposure to ultraviolet light.
Figure 8C:
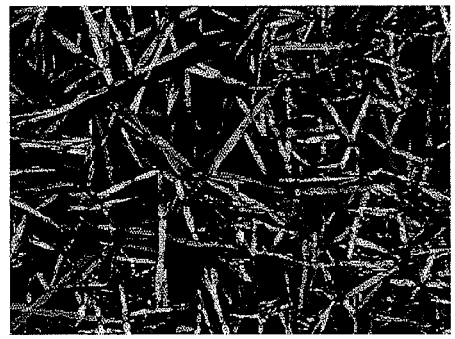
FIG. 8C shows a polarizing optical micrograph of Liquid Crystalline Compound 2 which have been heated to a temperature of 100° C. then cooled to a temperature of 25° C. after the first exposure to ultraviolet light.
Figure 8D:
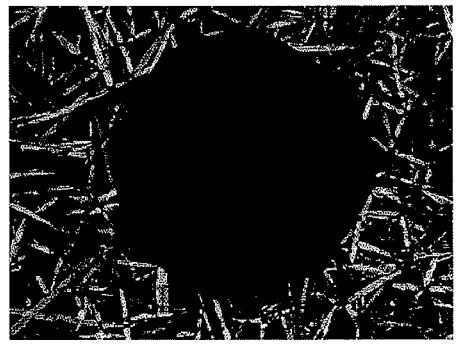
FIG. 8D shows a polarizing optical micrograph of Liquid Crystalline Compound 2 at a temperature of 25° C. after the second exposure to ultraviolet light.

According to the above-described procedure except that the observing temperature was changed to 25° C. Liquid Crystalline Compounds 1 and 2 were filled into a glass sandwich cell and irradiated with ultraviolet light under observation with polarizing optical microscope. FIGS. 7 and 8 are polarizing optical micrographs of phase transition between a crystalline phase and an isotropic phase of Liquid Crystalline Compounds 1 and 2, respectively. FIGS. 7A and 8A are polarizing optical micrographs of the crystalline phase at a temperature of 25° C. FIGS. 7B and 8B are polarizing optical micrographs of the state where the compounds are exposed to ultraviolet light at a temperature of 25° C. FIGS. 7C and 8C are polarizing optical micrographs of the state where, after the exposure to ultraviolet light, the cells have been heated to a temperature of 100° C. then cooled to a temperature of 25° C. FIGS. 7D and 8D are polarizing optical micrographs of the state where the compounds are second exposed to ultraviolet light at the cooled state to a temperature of 25° C.

In both of Liquid Crystalline Compounds 1 and 2, isomerization, and phase transition from a crystalline phase (Cry) to an isotropic phase (Iso) were induced by the exposure to ultraviolet light at a temperature of 25° C., and a dark field was observed in crossed nicols observation (FIGS. 7B and 8B).

Subsequently, the samples that partially underwent phase transition to the isotropic phase were heated to 100° C. and then cooled to 25° C. Then, the part where had underwent the phase transition to the isotropic phase was transformed to the crystalline phase (Cry) again (FIGS. 7C and 8C). Further, when the sample in which the whole had become the crystalline phase (Cry) was exposed to ultraviolet light for the second time, isomerization, and phase transition from a crystalline phase (Cry) to an isotropic phase (Iso) were induced, and a dark field was observed in crossed nicols observation (FIGS. 7D and 8D), similarly to the first exposure to ultraviolet light. These phenomena were observed in both of Liquid Crystalline Compounds 1 and 2. This result shows that the phase transition between the crystalline phase and the isotropic phase of these compounds is reversible, and that photosensitive material capable of repeated use can be produced from these compounds.

Example 2

Figure 9A:
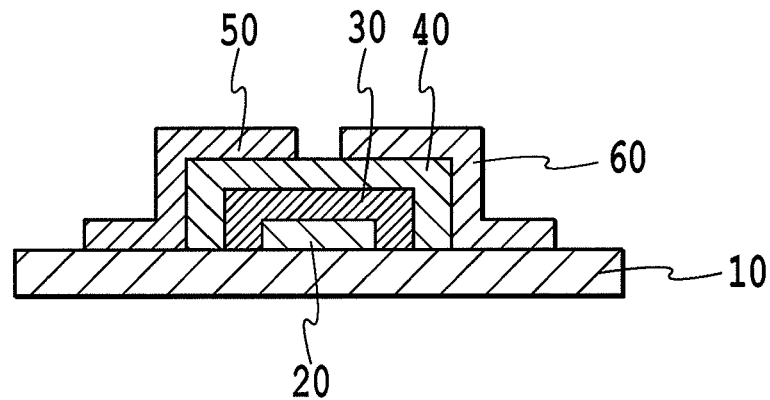
FIG. 9A shows a constitutional example of TFT elements of top-contact type comprising the liquid crystalline compounds of the present invention.
Figure 9B:
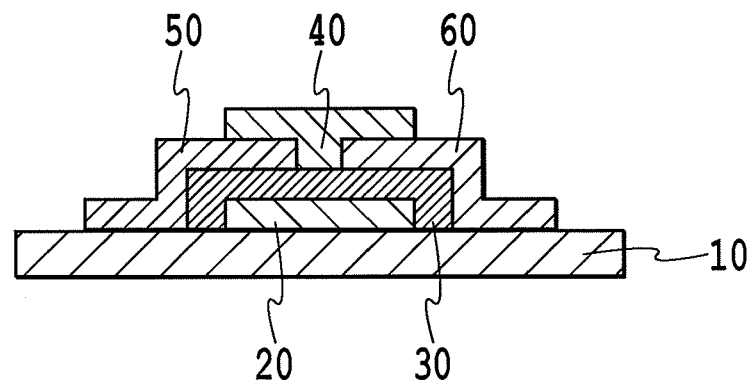
FIG. 9B shows a constitutional example of TFT elements of bottom-contact type comprising the liquid crystalline compounds of the present invention.
Figure 9C:
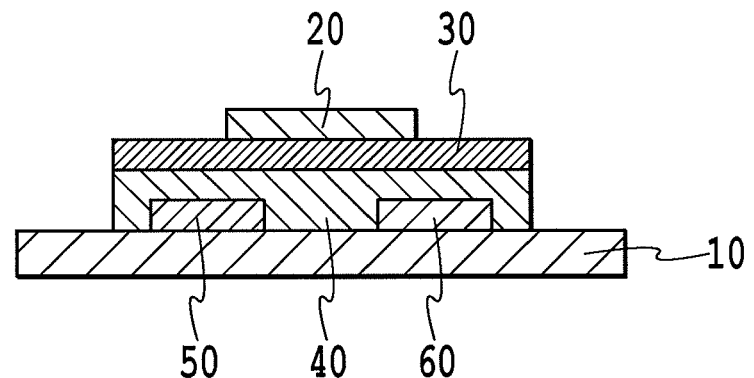
FIG. 9C shows a constitutional example of TFT elements of top-gate type comprising the liquid crystalline compounds of the present invention.

FIGS. 9A-9C show constitutional examples of TFT elements produced from the liquid crystalline compounds of the present invention. The top-contact type TFT element shown in FIG. 9A has substrate 10, gate electrode 20 on the substrate 10, gate insulation film 30 covering the gate electrode 20, organic semiconductor layer 40 covering the gate insulation film 30, and source electrode 50 and drain electrode 60 formed on the organic semiconductor layer 40. Here, either of the organic semiconductor layer 40 or the gate insulation film 30 can be formed from the liquid crystalline compounds of the present invention. It become possible to control the electrical properties of the TFT elements by exposing the organic semiconductor layer 40 or the gate insulation film 30, which has been formed from the liquid crystalline compounds of the present invention, to ultraviolet or visible light.

FIG. 9B shows a constitutional example of a bottom-contact type TFT element. The constitution shown in FIG. 9 is different from the element shown in FIG. 9A in the following points: source electrode 50 and drain electrode 60 being in contact with gate insulation film 30, and the gate insulation film 30, the source electrode 50 and the drain electrode 60 being in contact with organic semiconductor layer 40. The effects of exposure of the element shown in FIG. 9B to light are similar to those of the element shown in FIG. 9A.

When the gate insulation film 30 is formed from the liquid crystalline compounds of the present invention in the elements shown in FIGS. 9A and 9B, it is necessary for the organic semiconductor layer 40 lying thereon to transmit the ultraviolet or visible light for use in control of properties of the TFT element in a sufficient intensity.

FIG. 9C shows a constitutional example of a top-gate type TFT element. The TFT element shown in FIG. 9C has substrate 10, source electrode 50 and drain electrode 60 which are disposed on the substrate 10 apart from each other, organic semiconductor layer 40 covering the source electrode 50 and the drain electrode 60, gate insulation film 30 formed on the organic semiconductor layer 40, and gate electrode 20 formed on the gate insulation film 30.

When the organic semiconductor layer 40 is formed from the liquid crystalline compounds of the present invention in the element shown in FIG. 9C, it is necessary for either of the substrate 10 or the laminated structure of the gate insulation film 30 and the gate electrode 20 to transmit the ultraviolet or visible light for use in control of properties of the TFT element in a sufficient intensity. Alternatively, when the gate insulation film 30 is formed from the liquid crystalline compounds of the present invention, it is necessary for either of the gate electrode 20 or the laminated structure of the substrate 10 and the organic semiconductor layer 40 to transmit the ultraviolet or visible light for use in control of properties of the TFT element in a sufficient intensity.

The substrate 10, the gate electrode 20, the source electrode 50 and the drain electrode 60 may be formed from any material known in the art. Further, the gate insulation film 30 and the organic semiconductor layer 40 may be formed from any material known in the art, when they are not formed from the liquid crystalline compounds of the present invention.

Example 3

Figure 10:
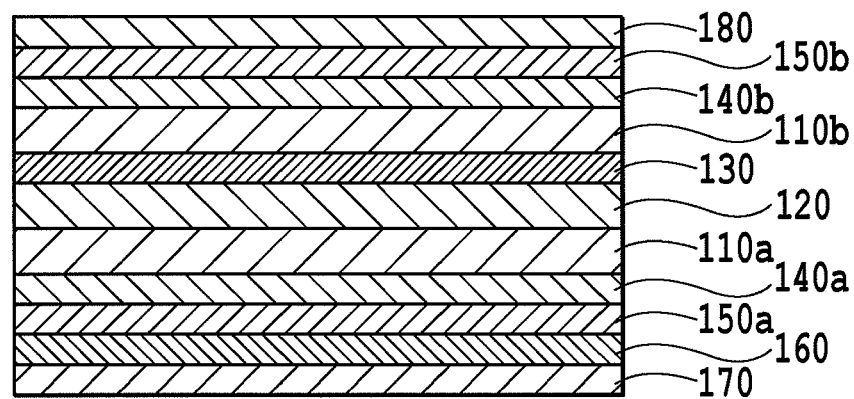
FIG. 10 shows a constitutional example of liquid crystalline display comprising the liquid crystalline compounds of the present invention.

FIG. 10 shows constitutional example of a liquid crystalline display produced from the liquid crystalline compounds of the present invention. The liquid crystalline display shown in FIG. 10 has a pair of transparent substrates 110(a, b), liquid crystalline layer 120 and color filter 130 disposed between the pair of transparent substrates 110(a, b), optical compensators 140(a, b) and polarizers 140 (a, b) respectively disposed on the outer surface of the pair of transparent substrates 110(a, b), anti-reflection layer 180 disposed on the surface of the polarizer 140b on the light exiting side, and brightness enhancement film 160 and light guide 170 disposed on the surface of the polarizer 140a on the side of a backlight (not shown). Here, the color filter 130, the optical compensators 140(a, b), the brightness enhancement film. 160, the light guide 170 and the anti-reflection layer 180 are optional layers which may be formed if necessary. Here, either of the liquid crystalline layer 120 or the optical compensators 140(a, b) can be formed from the liquid crystalline compounds of the present invention.

When the liquid crystalline layer 120 is formed from the liquid crystalline compounds of the present invention, it becomes possible to change the indicated content on the display by position-selective exposure to ultraviolet or visible light.

Alternatively, when the optical compensators 140(a, b) are formed from the liquid crystalline compounds of the present invention, it becomes possible to control viewing angle property or indicating color by exposure to ultraviolet or visible light. Besides, the liquid crystalline layer 120 can be formed from conventional calamitic liquid crystalline molecules, in this case. Moreover, means for applying electrical field (such as electrodes) for controlling the orientation state of the liquid crystalline molecules to change indicated content may be disposed on the transparent substrates 110(a, b).

REFERENCE SIGNS LIST 10 substrate
20 gate electrode
30 gate insulation film
40 organic semiconductor layer
50 source electrode
60 drain electrode
110(a, b) transparent substrate
120 liquid crystalline layer
130 color filter
140(a, b) optical compensator
150(a, b) polarizer
160 brightness enhancement film
170 light guide
180 anti-reflection layer

The invention claimed is:

1. A liquid crystalline compound represented by general formula (1):

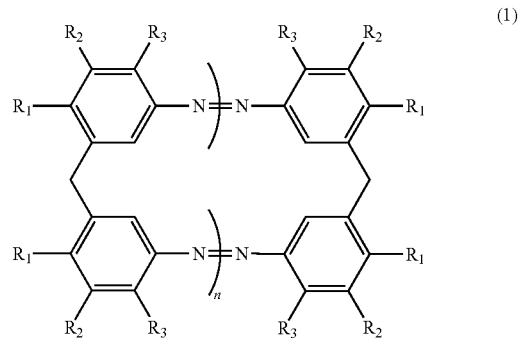

wherein:
$R^1$, $R^2$ and $R^3$ are independently selected from the group consisting of hydrogen, alkyl, alkoxyl, alkoxycarbonyl, alkoxycarbonyloxy, alkanoyl, alkanoyloxy, alkoxyphenyl, and N-alkylaminocarbonyl; and
n is an integer of 1 to 4,
with the proviso that the case where all of $R^1$, $R^2$ and $R^3$ are hydrogen is excluded.

2. An optical element comprising the liquid crystalline compound according to claim 1.

3. A photosensitive material comprising the liquid crystalline compound according to claim 1.

4. The photosensitive material according to claim 3 applied to photo-patternable material, photosensitive ink, or a photosensitive adhesive.

* * * * *